US008282982B2

(12) United States Patent
Kirkpatrick et al.

(10) Patent No.: US 8,282,982 B2

(45) Date of Patent: Oct. 9, 2012

(54) METHOD AND SYSTEM FOR COATING A SURFACE OF A MEDICAL DEVICE WITH A THERAPEUTIC AGENT AND DRUG ELUTING MEDICAL DEVICES MADE THEREBY

(75) Inventors: Sean R. Kirkpatrick, Littleton, MA (US); Richard C. Svrluga, Newton, MA (US)

(73) Assignee: Exogenesis Corporation, Billerica, MA (US)

( * ) Notice: Subject to any disclaimer, the term of this patent is extended or adjusted under 35 U.S.C. 154(b) by 821 days.

(21) Appl. No.: 12/243,285

(22) Filed: Oct. 1, 2008

(65) Prior Publication Data

US 2009/0098186 A1 Apr. 16, 2009

Related U.S. Application Data

(60) Provisional application No. 60/976,685, filed on Oct. 1, 2007, provisional application No. 61/024,719, filed on Jan. 30, 2008.

(51) Int. Cl.
*A61L 33/00* (2006.01)

(52) U.S. Cl. ....... 427/2.24; 427/2.25; 427/523; 427/534

(58) Field of Classification Search ................. 427/2.24, 427/2.25, 523, 534
See application file for complete search history.

(56) References Cited

U.S. PATENT DOCUMENTS

| | | | | |
|---|---|---|---|---|
| 5,811,151 | A * | 9/1998 | Hendriks et al. | 427/2.24 |
| 6,743,463 | B2 * | 6/2004 | Weber et al. | 427/2.24 |
| 7,105,199 | B2 * | 9/2006 | Blinn et al. | 427/2.24 |
| 2006/0204534 | A1 | 9/2006 | Blinn et al. | |
| 2007/0087034 | A1 | 4/2007 | Blinn et al. | |

OTHER PUBLICATIONS

International Search Reported dated Apr. 14, 2006 for PCT/US08/78429. Applicant: Exogenesis Corporation.
Written Opinion dated Apr. 14, 2006 for PCT/US08/78429. Applicant: Exogenesis Corporation.
International Preliminary Report on Patentability dated Apr. 7, 2010 for PCT/US08/78429. Applicant: Exogenesis Corporation.
Supplementary European Search Report dated Jan. 18, 2012 for European Patent Application No. 08836587.9.

* cited by examiner

*Primary Examiner* — Eisa Elhilo

(74) *Attorney, Agent, or Firm* — Burns & Levinson LLP; Jerry Cohen; David W. Gomes

(57) ABSTRACT

A multi-layer drug coated medical device such as for example an expandable vascular drug eluting stent is formed by vacuum pulse spray techniques wherein each layer is irradiated to improve adhesion and/or drug elution properties prior to formation of subsequent layers. Layers may be homogeneous or of diverse drugs. Layers may incorporate a non-polymer elution-retarding material. Layers may alternate with one or more layers of non-polymer elution-retarding materials. Polymer binders and/or matrices are not used in the formation of the coatings, yet the pure drug coatings have good mechanical and elution rate properties. Systems, methods and medical device articles are disclosed.

28 Claims, 6 Drawing Sheets

METHOD AND SYSTEM FOR COATING A SURFACE OF A MEDICAL DEVICE WITH A THERAPEUTIC AGENT AND DRUG ELUTING MEDICAL DEVICES MADE THEREBY

REFERENCE TO RELATED APPLICATIONS

This application claims priority from U.S. Provisional Patent Application No. 60/976,685, filed Oct. 1, 2007 by Sean R. Kirkpatrick et al. and entitled Therapeutic Agent and Drug Eluting Medical Devices Made Thereby, and from U.S. Provisional Patent Application No. 61/024,719, filed Jan. 30, 2008 by Sean R. Kirkpatrick et al. and entitled Therapeutic Agent and Drug Eluting Medical Devices Made Thereby. The contents of both applications are hereby incorporated herein by reference.

FIELD OF THE INVENTION

This invention relates generally to medical devices intended for implant in a mammal and, more particularly to a method and system for forming a drug eluting coating on a medical device avoiding the necessity of using a polymer matrix to retain the drug or control its elution properties.

BACKGROUND OF THE INVENTION

Medical devices intended for implant into the body or bodily tissues of a mammal (including a human), as for example medical prostheses or surgical implants, may be fabricated from a variety of materials including various metals, metal alloys, plastic or polymer materials, solid resin materials, glassy materials and other materials including various biodegradable materials as may be suitable for the application and appropriately biocompatible. As examples, certain stainless steel alloys and cobalt-chrome alloys have been used. Such devices include for example, without limitation, vascular stents and artificial joint prostheses, etc. It has often been found beneficial to coat the surfaces of such devices with a therapeutic agent such as a medicine or drug to increase the likelihood of a successful outcome for the surgical implant treatment.

For example, in the case of an implantable vascular stent, it is often desirable to apply drugs to the surface of the stent prior to its introduction into a vascular vessel. Implantable vascular stents may be fabricated from metal materials or may be fabricated from biodegradable materials. In the past, it has been the experience that therapeutic drugs, when applied directly to an expandable vascular stent, are not as effective as intended. Sometimes, the therapeutic agent is released (elutes) from the surface too rapidly (perhaps even washing off almost entirely during implantation of the stent. Other times the stent-drug combination does not withstand the mechanical stresses imposed during compression, expansion, or flexing of the stent required before and during implantation and the drug coat cracks, flakes, or delaminates during mechanical deformation—this generally results in either loss of the drug, or an undesirable change in the rate at which it elutes, following implantation. Especially when larger drug loads requiring thicker coatings are indicated, the problem of retaining an undamaged drug coating on the stent during and following mechanical strains has been problematical. It has become a common practice to use a polymer matrix to bond the therapeutic agent to such stents or to encapsulate the drug both to improve the durability and ductility of the coating and to help control the in-situ drug elution rate. It is now believed that such polymers have undesirable side effects that can result in unfavorable outcomes. There is a need for a drug-coated expandable vascular stent that doesn't employ a polymer or other binder matrix to control mechanical and elution properties, but where a robust and durable drug coating is applied directly on the bare stent in a manner that provides a suitable elution rate and which withstands the normal mechanical activities necessary to implant the stent without shedding or unacceptably compromising the coating.

Many methods are known for coating surgical implants with drugs or drug-polymer matrices. Among these, dipping and spray applications have been commonly used and various spray techniques have been employed. Usual spray techniques have involved dissolving one or more therapeutic agents and perhaps including a polymer matrix material in a solvent to form a solution with suitable properties for spray application. WIPO patent application publication WO06086693A2 published Aug. 17, 2006 (Brown) describes an apparatus for vacuum spraying medical devices with a drug-polymer coating using an ultrasonic nozzle. In U.S. Pat. No. 7,198,675 granted Apr. 3, 2007 Fox et al. describe mounting a bare stent on a mandrel fixture and spray-coating selective surfaces of the stent by spraying a solvent, drug, polymer, or combination of any of solvent, drug, and polymer. Still, the clinical problem remains that vascular stents coated with drug alone have not performed well and drug-polymer combinations have introduced undesired side effects.

When many drugs are coated onto expandable stents, it is seen that a single application cannot apply the necessary drug load needed for the desired therapy to be effective. With thick coatings, there are difficulties in removing the solvent without undesirable effects. By using multiple layer coatings, greater drug loads can be applied to a stent as taught in U.S. Pat. No. 5,464,650 granted Nov. 7, 1995 to Berg et al. but such multi-layer coatings have been most successful with drug-polymer matrix coatings. Compared to multi-layer drug-polymer matrix coatings, the multi-layer drug-only coatings, being thicker, are more brittle and have less strength and so have tended to crack and delaminate more severely when the stents are flexed, expanded or subjected to other mechanical strains.

Gas cluster ion beams (GCIB) are known, and have been used to process surfaces for purposes of cleaning, etching, smoothing, film growth, and the like. Gas cluster ions are ionized, loosely bound, aggregates of materials that are normally gaseous under conditions of standard temperature and pressure—typically consisting of from a few hundreds atoms or molecules to as many as a few ten thousands of atoms or molecules. Gas cluster ions can be accelerated by electric fields to considerable energies of thousands of keV. However because of the large number of atoms or molecules in each gas cluster ion, and because of the loose binding, their effect upon striking a surface is very shallow—the cluster is disrupted at impact and each atom or molecule carries only a few eV of energy. At the surface, instantaneous temperatures and pressures can be very high at gas cluster ion impact sites, and a variety of surface chemistry, etching, and cleaning effects can occur. Gas cluster ion beams have been used to clean and smooth medical implants and to adhere drugs to the surfaces of medical devices including stents (See U.S. Pat. No. 7,105,199 granted Sep. 12, 2006 to Blinn et al. and U.S. Pat. No. 6,676,989, granted Jan. 13, 2004 to Kirkpatrick et al.)

It is therefore an object of this invention to provide methods and systems for coating medical devices such as expandable vascular stents with drugs without the necessity of a polymer coat or matrix to promote durability and to control elution rate.

It is a further object of this invention to provide methods and systems for forming multi-layer drug coatings for medical devices that are durable, have controlled drug elution rates, and are well adhered.

A still further object of this invention to provide methods and systems for controlling the elution rate of a drug coating on a medical device by irradiation of the drug coating.

Another object of this invention to provide a drug-eluting medical device, as for example an expandable vascular stent that is polymer-free and, which has a drug coating having a controlled dose as a durable coating or durable multi-layer coating.

An additional object of this invention is to provide a drug-eluting medical device with controlled elution rate and to provide methods and systems for controlling an elution rate of a drug coating on a medical device by incorporating an elution-retarding material within the drug coating and irradiating the drug coating with the incorporated elution-retarding material.

SUMMARY OF THE INVENTION

The objects set forth above as well as further and other objects and advantages of the present invention are achieved by the invention described hereinbelow.

The present invention provides methods and systems for forming coatings on medical devices, as for example expandable vascular stents. Drugs or other therapeutic agents are sprayed onto clean surfaces in a vacuum using systems and techniques that result in the ability to form coatings that are well adhered, durable, and resistant to shedding, delamination, and/or damage by mechanical strains such are commonplace in expandable vascular stents. Furthermore the invention provides the capability of multi-layer coatings that are well adhered and durable and able, by virtue of multiple layers, to incorporate increased drug dosages in the coating. A major advantage enjoyed by the invention is that it is not necessary to employ a polymer matrix, polymer binder, or polymer encapsulant to retain or strengthen the drug coating—thus the unwanted side effects now known to result from polymer use are avoided. The drug coating can be a substantially pure single drug, a mixture of drugs soluble in the same solvent, or a composite of drugs soluble in different solvents, but alternately layered in multiple layers.

The medical device is preferably cleaned by gas cluster ion beam processing. Then the drug is applied to the medical device surface by programmed pulsed high velocity spray deposition in a vacuum. The drug is preferably a solid that can be dissolved in a suitable solvent to form a sprayable liquid. One or more spray pulses form a thin layer on the medical device surface. For substantially cylindrical medical devices like a vascular stent, a fixture rotates the device during spray so that all desired surfaces are spray coated. Between successive spray pulses the solvent is vacuum evaporated, leaving only pure drug coating on the medical device surface. By controlling the spray geometry and pulse timing, the coating texture is controlled to produce either a smooth or a textured coating. After a predetermined number of spray pulses, the coating is irradiated, preferably by gas cluster ion beam bombardment, to improve adhesion of the coating and/or to convert the surface of the coating to a form that has a reduced elution rate when implanted into the body or tissues of a mammal. By repeating the coating process, multi-layer coatings can be built to provide coatings with increased drug doses in thicker coatings. A textured coating resulting from a preferred spray geometry has superior strength, durability and adhesion characteristics and provides good coating retention and elution rates following mechanical strain as is commonly experienced when expandable vascular stents are compressed, expanded, or flexed in preparation for or during their insertion and implantation.

One embodiment of the present invention provides a method of coating a medical device with a drug, comprising the steps of: disposing the medical device in a vacuum environment; providing a solution of a drug solute dissolved in a liquid solvent; spraying at least one pulse of the solution onto a surface of the medical device to form a solution coating on at least a portion of the medical device; vacuum treating the solution coating after the step of spraying to remove the solvent and leave a drug coating on the medical device; and treating the drug coating to enhance adhesion of the drug coating to the medical device surface and/or to retard drug transfer from the drug coating under intended usage conditions.

The steps of spraying and vacuum treating the solution coating may be repeated prior to the step of treating the drug coating. The method may further comprise repeating at least once, the steps of spraying, vacuum treating and treating the drug coating to thicken the drug coating.

The step of vacuum treating may include operating a vacuum pump connected to the vacuum environment to automatically reestablish vacuum pressures after each spraying pulse. The step of spraying may be adapted to deliver the solution to the medical device with only limited evaporation of the solvent. The step of spraying may be adapted to retain substantially all of the solute in solution until it reaches the medical device.

The drug coating step may comprise ion irradiating the drug coating in a manner to reduce a drug elution rate of the drug coating and/or to improve the adhesion of the drug coating to the medical device. The step of ion irradiating may comprise GCIB irradiation.

The method may further comprise the step of cleaning the medical device by gas cluster ion beam processing in a vacuum environment prior to the spraying step. The method may be used to coat substantially all medical device surface portions intended for mammalian body contact. The medical device may be a stent. The drug solution may comprise an elution-retarding material solute. The elution-retarding material solute may include one or more of a vitamin, a tocopherol, retinol, a retinoid, and a fat soluble biocompatible material.

In another embodiment, an apparatus for coating a medical device with a drug comprises: a vacuum chamber; means for holding the medical device in the vacuum chamber; means for pulse spraying a solution of the drug onto a surface of the medical device in the vacuum chamber to form a solution coating; vacuum producing means for providing a reduced pressure in the vacuum chamber for evaporating solvent from the solution coating to form a drug coating; and means for introducing a gas cluster ion beam into the vacuum chamber adapted to irradiate at least a portion of the drug coating with gas cluster ions.

The means for holding, means for pulse spraying and means for introducing may be constructed and adapted for full surface coating of the medical device. The apparatus may further comprise control means adapted to cause a sequence of spray pulses of the solution separated by evaporation periods for evaporating solvent from the solution coating from each spray pulse. The control means may be further adapted for causing sequential layers of drug coating to be separately irradiated with the gas cluster ion beam. The means for spraying may be adapted to deliver the solution to the medical device with only limited evaporation of the solvent.

In yet another embodiment, a drug coated medical device has at least one GCIB irradiated drug coating comprising a drug and an elution-retarding material. The coating may include one or more layers, and the drug and the elution-retarding material may be either contained in the same layer or in separate layers. The elution-retarding material may include one or more of a vitamin, a tocopherol, retinol, a retinoid, and a fat soluble biocompatible material.

For a better understanding of the present invention, together with other and further objects thereof, reference is made to the accompanying drawings and detailed description and its scope will be pointed out in the appended claims.

DETAILED DESCRIPTION OF THE PREFERRED METHODS AND EMBODIMENTS

Figure 1:
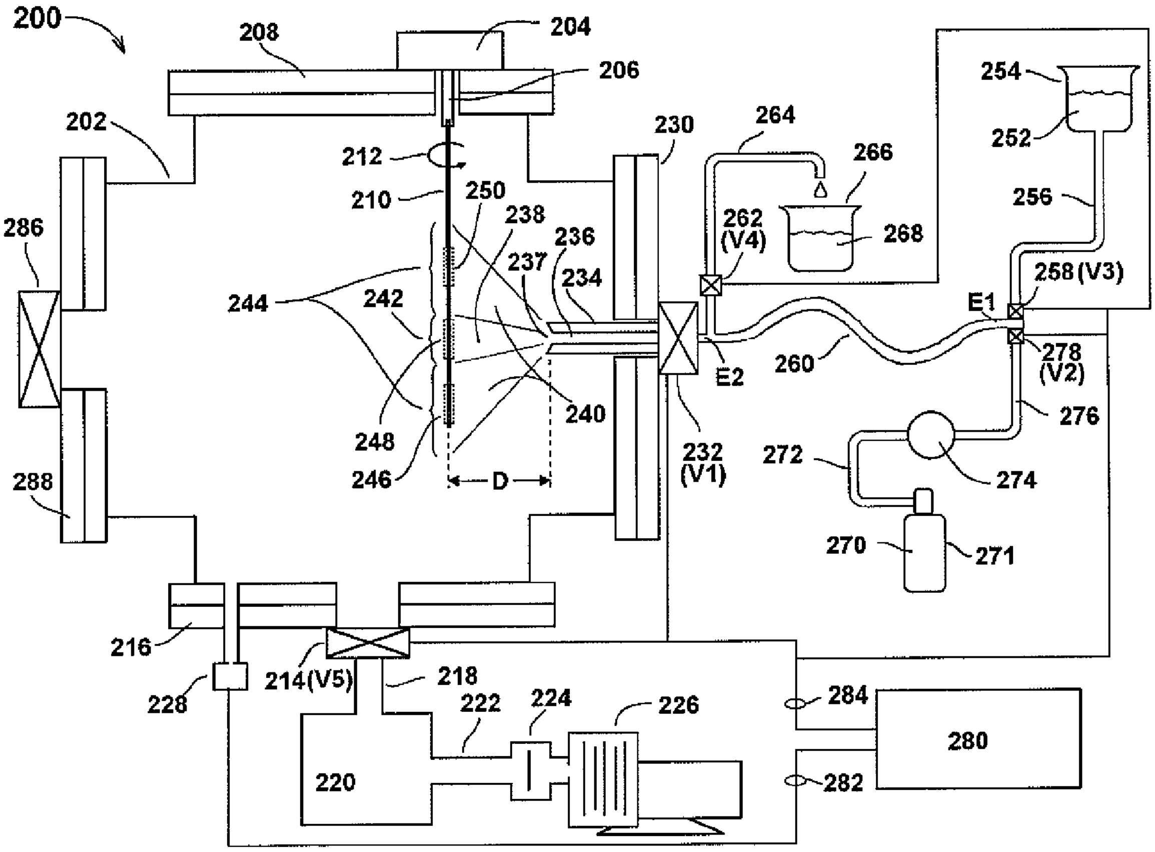
FIG. 1 is a schematic view of a vacuum spray coating system for medical devices according to an embodiment of the invention.

Reference is made to FIG. 1 of the drawings, which shows a system 200 for vacuum spray coating of a medical device according to an embodiment of the invention. FIG. 1 is a schematic view and dimensions are not drawn to scale. This system has two modes of use according to separate methods of the invention and is able to produce drug coatings on medical devices that are either smooth or textured coatings. The system includes a vacuum coating chamber 202 with multiple ports having flanges sealed by component mounting plates 208, 216, 230, and 288. The chamber 202 preferably has a volume of about 200 to 400 cubic inches. One of the ports has a component mounting plate 208 that mounts a motor 204 having a rotary shaft 206, which attaches a mandrel 210 so that the mandrel can be rotated about its axis with a rotary motion 212. The mandrel is adapted to hold cylindrical medical devices, as for example expandable vascular stents 246, 248, and 250 by passing through the bore of the stents and retaining them by friction fit or by means of clips or collars not shown. Although, for simplicity, a mandrel supporting the stents or other tubular or cylindrical medical devices by the inside diameter, it will be immediately understood by those skilled in the arts that other rotating supports are readily provided that will support an expandable mesh vascular stent in such a way that the inside diameter surfaces of the, stent can also be coated if necessary, by spraying through the mesh of the stent to impact the inside surface. It will also be appreciated that flat or otherwise shaped surfaces can also be spray coated by the apparatus by substituting appropriate holders for the medical devices using techniques well known in the arts. Using the rotating mandrel 210, the stents 246, 248, and 250 can be rotated about their axes by the rotary motion 212 provided by motor 204 to facilitate spray coating of the entire outer surface of the stents. The motor may rotate at any suitable rate, for example about 6 RPM.

A vacuum system operates the coating chamber 202 at a reduced pressure. Vacuum pump 226 may be a rough vacuum pump such as for example a Leybold D65B having a pumping speed of 54 CFM, for example. A high pumping speed of 50 CFM or more with an ultimate pressure capability below 35 mtorr is preferred. Vacuum pump 226 is coupled to the coating chamber 202 through a filter 224, a pumping line 222, a vacuum reservoir 220, additional pumping line 218, and a control valve (V5) 214. The vacuum reservoir may be a separate volume as indicated or may be formed assuring that pumping lines 218 and 222 have adequate volume to act as a reservoir to improve the rate of evacuating the coating chamber 202 when it receives a pressure burst (as will be discussed below. It is preferable that the reservoir should have a volume greater than the volume of the coating chamber 202, preferably 2 to 6 times the volume of the chamber 202. The control valve 214 is preferably a valve of a type that can be remotely actuated, preferably electrically or electro-pneumatically actuated.

One of the ports in the chamber 202 has a component mounting plate 288 with an opening through a gate valve 286, provided for connecting the chamber with other equipment as will be discussed hereinafter.

One of the ports in the chamber 202 has a component mounting plate 230 with an opening for a spray nozzle 234. The spray nozzle connects to a spray control valve (V1) 232, which is preferably a fast acting valve of a type that can be remotely actuated, preferably electrically actuated or electro-pneumatically actuated. A liquid reservoir 254 holds a liquid 252 for spray coating medical devices in the chamber 202. The liquid 252 is preferably a liquid solution of a normally solid therapeutic material, for example a drug such as rapamycin, or paclitaxel. A volatile solvent compatible with the therapeutic material, as for example tetrahydrofuran (THF), holds the therapeutic material in solution, forming the liquid 252. The liquid reservoir 254 connects through tubing 256 to a filling control valve 258 for delivering the liquid 252 to a first end (E1) of liquid storage loop 260. The filling control valve (V3) 258 is preferably a high-speed valve of a type that can be remotely actuated, preferably electrically actuated or electro-pneumatically actuated.

A pressurized gas 270 in a gas bottle 271 can flow through gas tubing 272 to an inlet of gas pressure regulator 274. The gas pressure regulator 274 is preferably adjustable and has an outlet connecting through gas tubing 276 to a gas control valve (V2) 278 for connecting to the first end (E1) of liquid storage loop 260. The gas control valve 278 is preferably a valve of a type that can be remotely actuated, preferably electrically actuated or electro-pneumatically actuated. The liquid storage loop 260 serves to store a predetermined amount of the liquid 252 for injecting into the nozzle 234 as a bolus, resulting in a pulse of liquid spray being ejected from the nozzle 234 into the chamber 202. A second end (E2) of liquid storage loop 260 connects to spray control valve (V1) and to overflow valve (V4). Both V1 and V4 are both preferably high-speed valves of types that can be remotely actuated, preferably electrically actuated or electro-pneumatically actuated. Valves V1, V2, V3, and V4 may optionally all be parts of a multi-port sample injection valve as for example a commercially available valve from the, Valco Instruments Co., Inc. model C22 Cheminert series. The liquid storage loop 260 may be tubing having a small internal diameter (eg.

0.0625 inches) and a predetermined length (eg. from about 1 inch to about 5 inches) to store a predetermined volume of liquid. For charging the liquid storage loop 260, V1 and V2 are closed and V3 and V4 are opened. Liquid 252 then flows by gravity out of the liquid reservoir 254 (although not shown, it will be understood that the liquid reservoir could be pressurized to promote flow, or that a metering pump could be used to promote and control the flow), through tubing 256 and V3 into and through liquid storage loop 260, filling the liquid storage loop 260, with overflow flowing through V4, through tubing 264 and into overflow reservoir 268 (with the overflow liquid 268 collecting in overflow reservoir 268). When liquid storage loop is charged, V3 and V4 are closed. V2 is then opened to pressurize the liquid charge in the liquid storage loop 260. Gas pressure regulator 274 may be set to provide a pressure of for example 0.5 PSI above atmospheric pressure. After the liquid storage loop is pressurized V2 remains open and V1 is opened, ejecting the stored volume in the liquid storage loop through the nozzle 234 causing it to expand into the vacuum in chamber 202. Nozzle 234 (Nozzle A) is an ultrasonic spray nozzle and may be a Sono-Tek Corporation model 8700-120 or similar ultrasonic nozzle having a nozzle bore 236 preferably in the range of from about 0.020 to about 0.030 inch diameter. The nozzle bore may optionally have a conical exit aperture with an included angle of about 118 degrees. More detailed description of the operation and timing of the V1, V2, V3, and V4 valve system operation and timing is discussed hereinafter in reference to FIG. 3.

Referring again to FIG. 1, the liquid 252 solution used for the spray is chosen based on the type of therapeutic agent that it is desired to coat onto the medical devices (eg. stents). For forming drug-eluting stents, rapamycin, paclitaxel, or other drugs that are soluble solids may be used. A compatible, low viscosity, volatile solvent, in which the drug remains stable for a workable period of time to allow coating, is used to form the liquid solution for spraying. THF is a preferred solvent, but, organic solvents such as ethanol, methanol, propylene glycol, polyethylene glycol, ethylene glycol, dimethylacetamide, dimethylsulfoxide, dimethylformamide, acetone, dichloromethane, as well as others are also suitable. The solution may be mixed in various predetermined concentrations of the therapeutic agent in the solvent based on the spray properties of the resulting liquid, the desired dose to be applied to the medical device, etc. For example, it has been found that rapamycin dissolved in THF can be successfully applied in a wide range of concentrations, preferably from about 1 mg/ml to about 10 mg/ml.

When the stored liquid volume in the liquid storage loop 260 is released through V1 and nozzle 234 a high velocity spray is explosively ejected into the vacuum in the chamber 202. The spray expands conically into the chamber 202 and strikes the mandrel 210 and medical devices (eg. stents 246, 248, 250) affixed thereto. The conical spray expansion has two parts. A first cone 238 has a smaller conical angle. A second cone 240 has a larger conical angle. The spray in the first cone 238 is a denser, coarser spray that makes little or no contact with the nozzle walls when it is blown out into the vacuum, the deposition spot it forms at the distance of the mandrel results in a qualitatively different coating. Without wishing to be bound by any particular theory in this regard, it is believed that the coarser particles arrive at the deposition spot in a wetter, form with less solvent evaporation occurring in transit, than is the case for the finer more diffuse spray that occurs in the portion of the second cone 240 that is outside of the first cone 238. Thus at the distance D of the mandrel 210 from the exit of the nozzle, there are two regions, a circular region 242, impacted by the coarser spray, and a larger annular region 244 impacted by the finer, more diffuse spray. The relative "wetness" and "dryness" of the spray at the distance of the mandrel 210 is also affected by the distance D between the nozzle exit aperture and the mandrel 210, on the volume of liquid dispensed in each spray pulse, the volatility of the solvent used, the concentration of the drug in the solvent, and the nozzle characteristics.

Medical devices may be processed in either the circular region 242 or in the annular region 244 with significantly different coating texture and quality results. When processed in the circular region with a relatively "wet" spray, a textured coating results. When processed in the annular region with a relatively "dryer" spray, a smooth coating results. When processed in the annular region with a spray that is too "dry" (perhaps the solvent evaporates almost entirely before reaching the medical device) a lumpy or cracked coating can result, more noticeably so with thicker coatings. When the spray is too "wet" then the coating can run or sag into the web structure of the stent creating "sails" or "webbing" that can crack or delaminate during expansion or bending of the stent. Thus, by choosing the processing region 242 or 244 and by choosing the distance D, one can control the "wetness" of the spray at the point of deposition on the medical device and thus control the type of coating that results (smooth or textured).

A controller 280, which may be a microprocessor based controller, a general purpose small computer, or other preferably programmable controller senses chamber 202 pressure through pressure sensor 228 and cable 282 and controls V1, V2, V3, V4, and V5 through cable 284 to control the vacuum in chamber 202 and to control the valve sequencing required to charge the liquid storage loop 260 and to eject the spray pulses into the chamber 202 for coating medical devices.

Table 1 shows conditions that produce coatings of various desirable types for an exemplary case of the drug rapamycin dissolved in THF. "Disp. Vol." is the dispensed volume per spray pulse, 8 spray pulse repetitions were made in forming the coating.

TABLE 1

| Case | Region | D (in) | Nozzle | Conc. (mg/ml) | Disp. Vol. (μl) | Coating |
|---|---|---|---|---|---|---|
| 1 | Circular | 1.38 | A | 4 | 140 | Textured, durable |
| 2 | Annular | 0.88 | A | 4 | 140 | Smooth |
| 3 | Circular | 0.88 | A | 4 | 140 | Sags & webbing |
| 4 | Annular | 1.88 | A | 4 | 140 | Lumps, cracks, poor adhesion |

Figure 2:
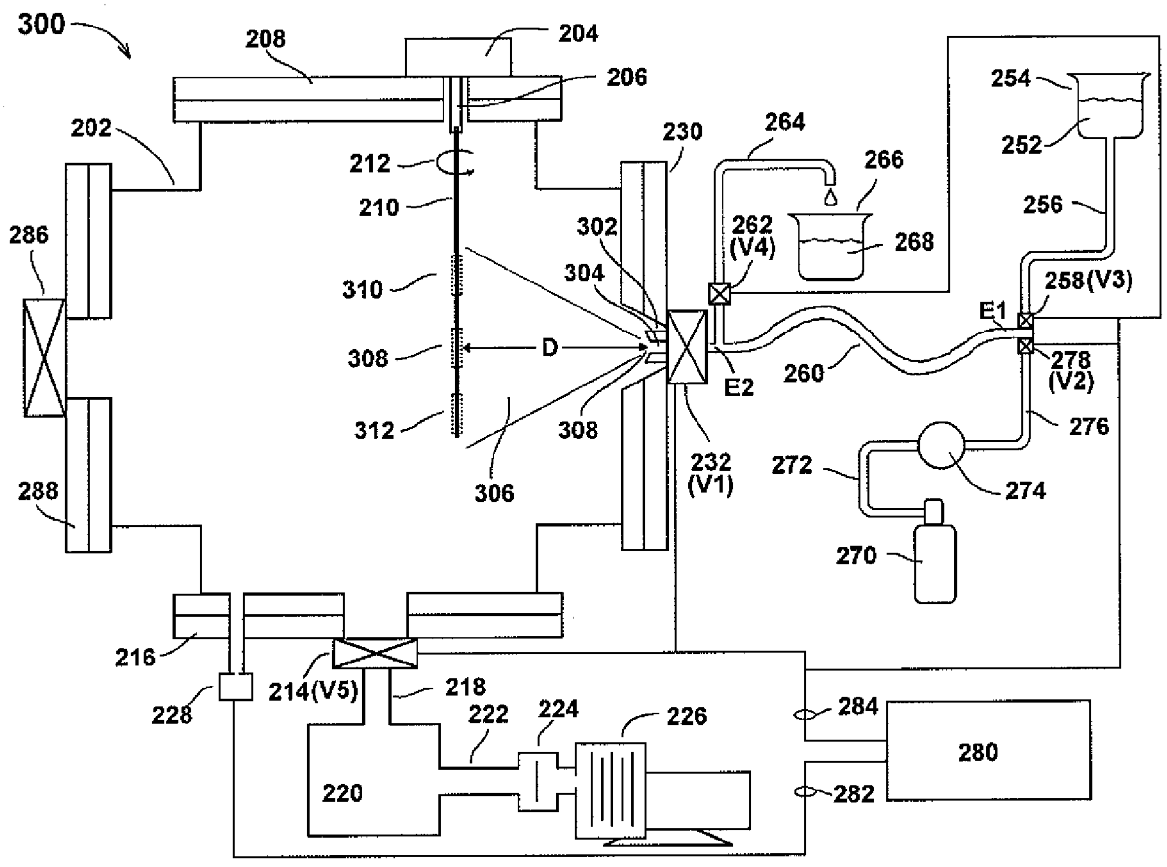
FIG. 2 is a schematic view of a vacuum spray coating system for medical devices according to an alternate embodiment of the invention.

Referring to FIG. 2 of the drawings in which like reference numbers refer to like features in FIG. 1, a system 300 for vacuum spray coating of a medical device according to an alternate embodiment of the invention is constructed similar to the the vacuum spray coating system 200 (FIG. 1) but differs in that it employs a short non-ultrasonic nozzle 302 (Nozzle B). FIG. 2 is a schematic view and dimensions are not drawn to scale. This system has two modes of use according to separate methods of the invention and is able to produce drug coatings on medical devices that are either smooth or textured coatings. Nozzle 302 has a cylindrical nozzle bore 304, which is about 0.5 inch long and about 0.093 inch inside diameter. The distance between the nozzle exit aperture 308 and the mandrel 210 is D. The nozzle exit aperture 308 may optionally be conical with an included angle of about 118 degrees. Nozzle B produces a large angle single cone spray expansion envelope 306 that produces a "wet" spray over a large processing region so that multiple medical devices (stents 308, 310, and 312) can be processed in the single spray cone. The "wetness" of the spray can be modified by changing the distance D, larger values of D producing "dryer" spray patterns at the mandrel 210.

Table 2 shows conditions that produce coatings of various desirable types for an exemplary case of the drug rapamycin dissolved in THF. "Disp. Vol." is the dispensed volume per spray pulse, 8 spray pulse repetitions were made in forming the coating.

TABLE 2

| Case | D (in) | Nozzle | Conc. (mg/ml) | Disp. Vol. (μl) | Coating |
|---|---|---|---|---|---|
| 5 | 1.63 | B | 4 | 140 | Textured, durable |
| 6 | 1.38 | B | 8 | 140 | Smooth |
| 7 | 0.88 | B | 4 | 140 | Sags & webbing |
| 8 | 2.5 | B | 4 | 140 | Lumps, cracks, poor adhesion |

Figure 3:
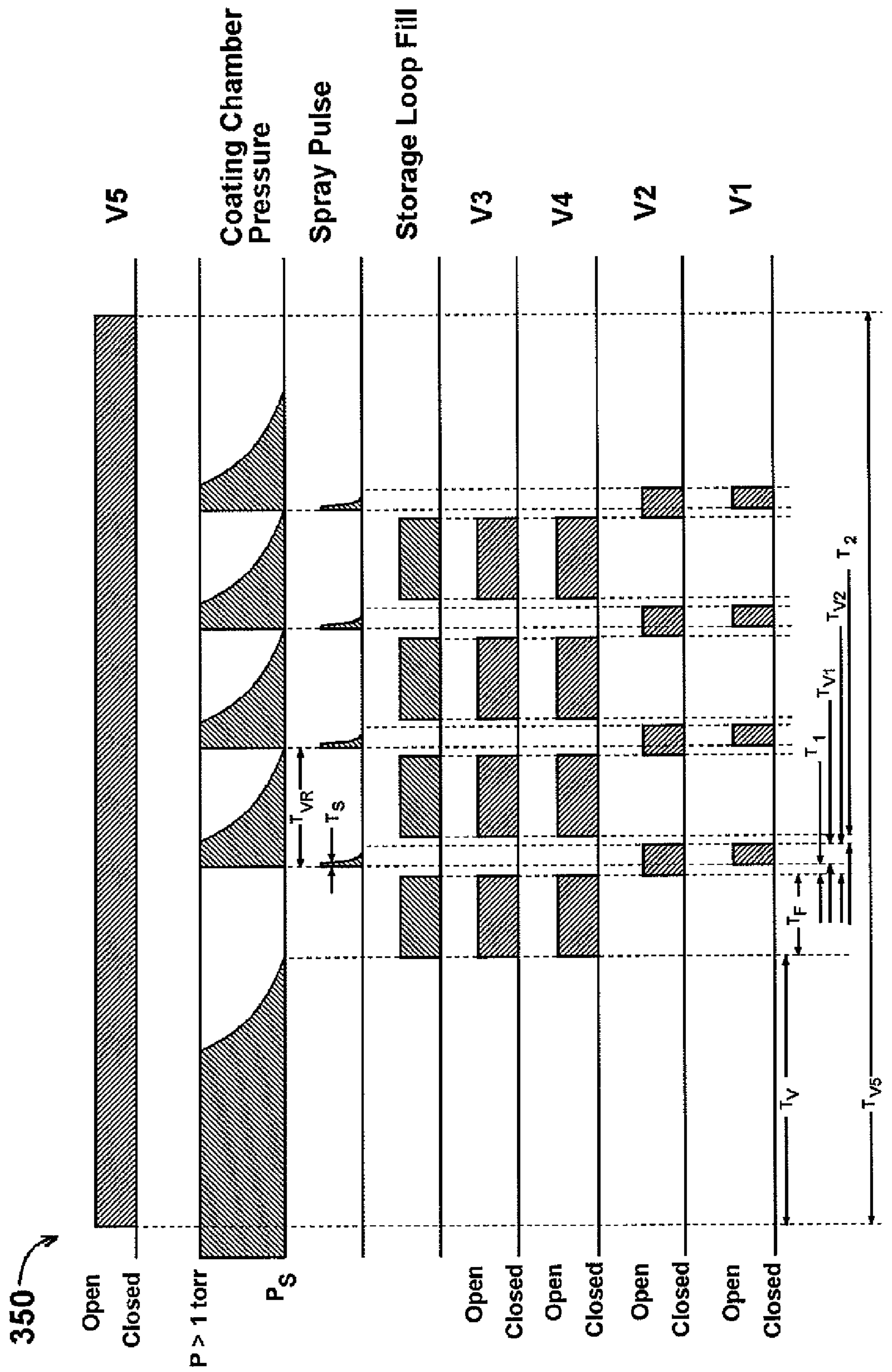
FIG. 3 is a timing diagram showing timing details for controlling pulse spray coating of a medical device according to the invention.

FIG. 3 of the drawings is a timing diagram 350 that is applicable to the spray control systems of both system 200 and system 300 discussed above. Timing diagram 350 shows the timing relationships of the actuations of valves V1, V2, V3, V4, and V5, and of the resulting changes in coating chamber pressure, spray pulses, and the filling and refilling of the liquid storage loop.

Coating a drug on a medical device such as a stent according to the invention is done by pulsed spraying of the liquid drug-solvent solution. The coatings are applied in layers. Each layer may be built by pulse spraying the medical device repetitively through the nozzle (Nozzle A or Nozzle B or other nozzle). Prior to coating a medical device (eg. a stent) it is preferable that the device be cleaned using gas cluster ion beam techniques as are taught in commonly owned U.S. Pat. No. 7,105,199 to Blinn et al. For cylindrical or tubular medical devices like vascular stents, generally multiple pulses of spray are applied while the stent rotates on the mandrel—this assures uniform coating on the outer surface of the stent. Four, eight, sixteen, or some other number of spray pulses may be applied for each layer of coating. A critical requirement of the method of the invention is that for each spray pulse, the flight time of the spray in the vacuum system be short enough that the atomized spray droplets arrive at the surface fast enough that the solvent in the liquid being sprayed has not completely evaporated before the droplets strike the medical device being coated. This permits the droplets to stick to the surface, where then the remaining solvent is rapidly vacuum evaporated. When the "wet" sprays are used, it is possible that the remaining solvent actually boils out of the coating, thus contributing to the texturing of the deposited coating. To maintain short flight time to assure solvent remains in the droplets as the reach the surfaces of the medical devices being coated it is necessary that a significant pressure differential exist across the nozzle during spraying. By operating the chamber 202 at a low pressure (vacuum of for example 35 mtorr) while pressuring the liquid being sprayed at about atmospheric pressure or above (for example about 0.5 psi above atmospheric pressure.) This assures that the bolus of liquid in the liquid storage loop explosively ejects into the vacuum at approximately sonic velocities. Thus the spray pulse is very short and intense. The continued pressure provided by the pressurized gas pressurizing the liquid bolus assures that all the liquid is quickly blown out of the storage loop and the nozzle so that the liquid does not evaporate in and clog the nozzle.

The timing of the spray pulses and the vacuum system performance is controlled to assure that essentially all the solvent evaporates, or boils off or flashes off after each spray pulse and before each subsequent spray pulse. After each multi-spray-pulse layer is applied, the coated medical device may be left in the vacuum system for several additional seconds to a few additional minutes to further assure that all the solvent is extracted from the layer. Each layer is then preferably processed by irradiating it to further improve the adhesion of the layer and to at least partially modify the surface of the coating to reduce it's solubility in mammalian bodily fluids (saline-like fluids) and to reduce the rate at which the drug coating elutes after surgical implant into a mammalian body or bodily tissue.

After irradiation, discussed further hereinbelow, the medical device (eg. a stent) may optionally have additional layers of drug added on previously applied layers, by repeating the multi-pulse-spray process for each layer. Following the addition of each layer the irradiation step is preferably also repeated. Each layer may consist of one or more drugs dissolved in a common solvent. For drugs that do not share a common solvent, or which are unstable when in solution together, subsequent layers may comprise different drugs and or different solvents. Thus complex layered drug coatings may be applied to medical devices.

The process for applying each layer consisting of one or multiple pulsed spray depositions is illustrated in timing diagram 350 of FIG. 3. Now refer to FIG. 3 for timing and to FIG. 1 and/or FIG. 2 for item designator numbers. The timing of V5 is shown in the line labeled V5 in timing diagram 350. At the beginning of each layer-coating step, V5 is opened for a period of time $T_{V5}$ to pump the chamber 202 to the desired vacuum condition for coating. To achieve this vacuum condition the pressure in the chamber 202 may be sensed and compared to a desired spraying pressure $P_S$. $P_S$ may preferably be on the order of 20 to 100 mtorr, for example 35 mtorr. After the V5 valve opens and after a period of time $T_V$, the coating chamber pressure reaches $P_S$ and V3 and V4 are opened for a programmed length of time, $T_F$, to fill the liquid storage loop 260 with liquid 252. TF may be for example about 17 seconds. At the end of TF, V3 and V4 are closed and V2 is opened for a period of time, TV2, to pressurize the liquid in the liquid storage loop 260 with a gas pressure that may be about 0.5 psi above atmospheric pressure. After a delay, T1, which may be about 1 second or longer, V1 is opened, permitting the pressurized liquid in the liquid storage loop to be sprayed abruptly into the chamber 202 through V1 and through nozzle 234 or nozzle 302. The spray pulse is shown on the timing diagram 350 line labeled "Spray Pulse" and is of a short duration TS which may be less than half a second. As the spray pulse of liquid and pressurized gas enters the chamber 202, the pressure in the coating chamber pressure rises sharply to a pressure level P that is considerably greater than one torr. After TV1, V1 closes and as the solvent in the sprayed liquid quickly evaporates, the coating chamber pressure falls rapidly under the influence of the vacuum pump 226 evacuating the chamber 202. After V1 closes and after a short delay T2, which may be about 1 second, the liquid storage loop charging sequence repeats, recharging the liquid storage loop 260. When essentially all the solvent has evaporated and been pumped away, the coating chamber pressure again falls to PS and when the liquid storage loop is recharged the pulse spray cycle repeats for a number of pulses programmed for each layer in controller 289 (shown as a total of four pulses in timing diagram 350). After the programmed number of spray pulses have been executed by controller 280, the controller maintains V5 open for an additional period of time to further assure that all solvent is vacuum evaporated from the coating layer. The additional period of time may be from several seconds to several minutes as required to assure drying and programmed in controller 280.

Once a layer has been coated onto the medical device (a smooth layer or a textured layer according to spray parameters and geometry as discussed above), the coating is preferably irradiated to modify the surface and to improve adhesion of the coating. Adhesion may be improved by gas cluster ion beam processing of the surface. The surface may be irradiated using a GCIB comprising Argon cluster ions or cluster ions of another inert gas. The GCIB is preferably accelerated with an accelerating potential of from 5 kV to 50 kV or more. The coating layer is preferably exposed to a GCIB dose of at least about $1\times10^{13}$ gas cluster ions per square centimeter. The effect of the GCIB irradiation is two-fold. It improves the adhesion of the coating to the surface of the stent (or to a prior coating) by shallow ion beam stitching or mixing of the coating layer to the surface. It also improves (increases) the drug elution time by converting the surface of the coating to a form that is less soluble in mammalian body fluids. The exact mechanism of this improvement is not known, but it is believed that the GCIB denatures a shallow uppermost layer of the surface, perhaps in such a way that the surface becomes partially converted to carbon (in cases where the coating is carbon-containing) and/or other low solubility materials, which form an at least partially encapsulating layer that slows the elution of the drug. Testing has shown such modified surfaces to be carbon rich. Nevertheless, substantial unmodified drug remains adhered to the medical device beneath the very shallow modified layer.

As an alternative to GCIB irradiation of the coating layers, it is also feasible to irradiate the deposited coating layers using conventional ion plasma processing techniques. The coating layer may be irradiated in a plasma processing tool as for example an Edwards model S123 DC sputter coater system. Other plasma processing systems can also be use for the irradiation. In an exemplary case, a 400V argon plasma at a pressure of 20 mbar (operating at 2 mA) irradiated a rapamycin coated surface and testing showed that the drug elution rate was significantly improved over an unirradiated control.

Thicker, slower and longer eluting drug coatings result when multiple layers are applied to a medical device and when those layers are irradiated between successive layers. Testing has also shown that the textured coatings formed using the "wetter" forms of pulse spraying according to embodiments of this invention are stronger, tougher, better adhered and more able to withstand the rigors of compressing, expanding and flexing of medical devices such as vascular stents. By using the methods of this invention, these benefits can be achieved without the necessity of employing polymer binders or matrices to retain the drugs on the medical devices. This has great importance because of the recent understanding that the polymers themselves can contribute side effects such as inducing thrombosis or otherwise impairing the favorable outcome anticipated when a decision is taken to resort to the use of surgical implants like expandable vascular stents to alleviate a medical condition.

Figure 4:
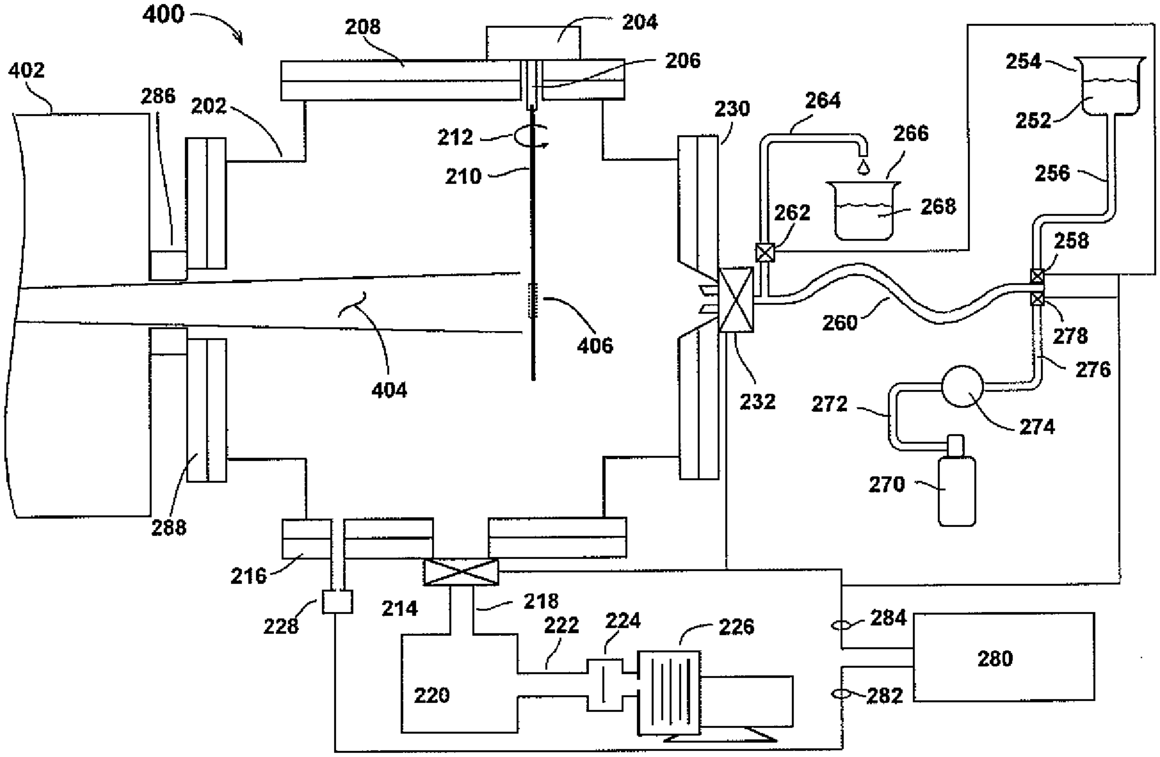
FIG. 4 schematic view of a vacuum spray coating system for medical devices having an integrated a gas-cluster ion beam processing system for producing coated medical devices according the invention.

Referring to FIG. 4 of the drawings in which like reference numbers refer to like features in FIGS. 1 and 2, a system 400 for vacuum spray coating of a medical device is constructed to have an integrated a gas-cluster ion beam processing system for producing coated medical devices according embodiments of the invention. FIG. 4 is a schematic view and dimensions are not drawn to scale. Although this system 400 shows a gas-cluster ion beam system integrated with a vacuum spray coating system similar to system 300, such integration of GCIB and spray coating functions and apparatus is equally applicable to a vacuum spray coating system similar to system 200. At component mounting plate 288, the gate valve 286 (shown in this schematic as open, not closed as it was in FIGS. 1 and 2) attaches the chamber 202 to a GCIB beam output portion of a GCIB processing system 402. After coating the medical device 406 (eg. a stent) in the coating chamber 202, according to the apparatus and methods taught hereinbefore, a GCIB 404 irradiates the medical device 406 while it is rotated by motor 204 to assure irradiation of all outer surfaces. The integration of GCIB processing and drug spray coating according to the methods of this invention facilitates formation of multiple layer coatings with minimal handling, minimal contamination, and reduced elapsed time compared to alternatives. Gate valve 286 may be closed during pulse spraying and spray control valve 232 may be closed during GCIB processing.

Figure 5:
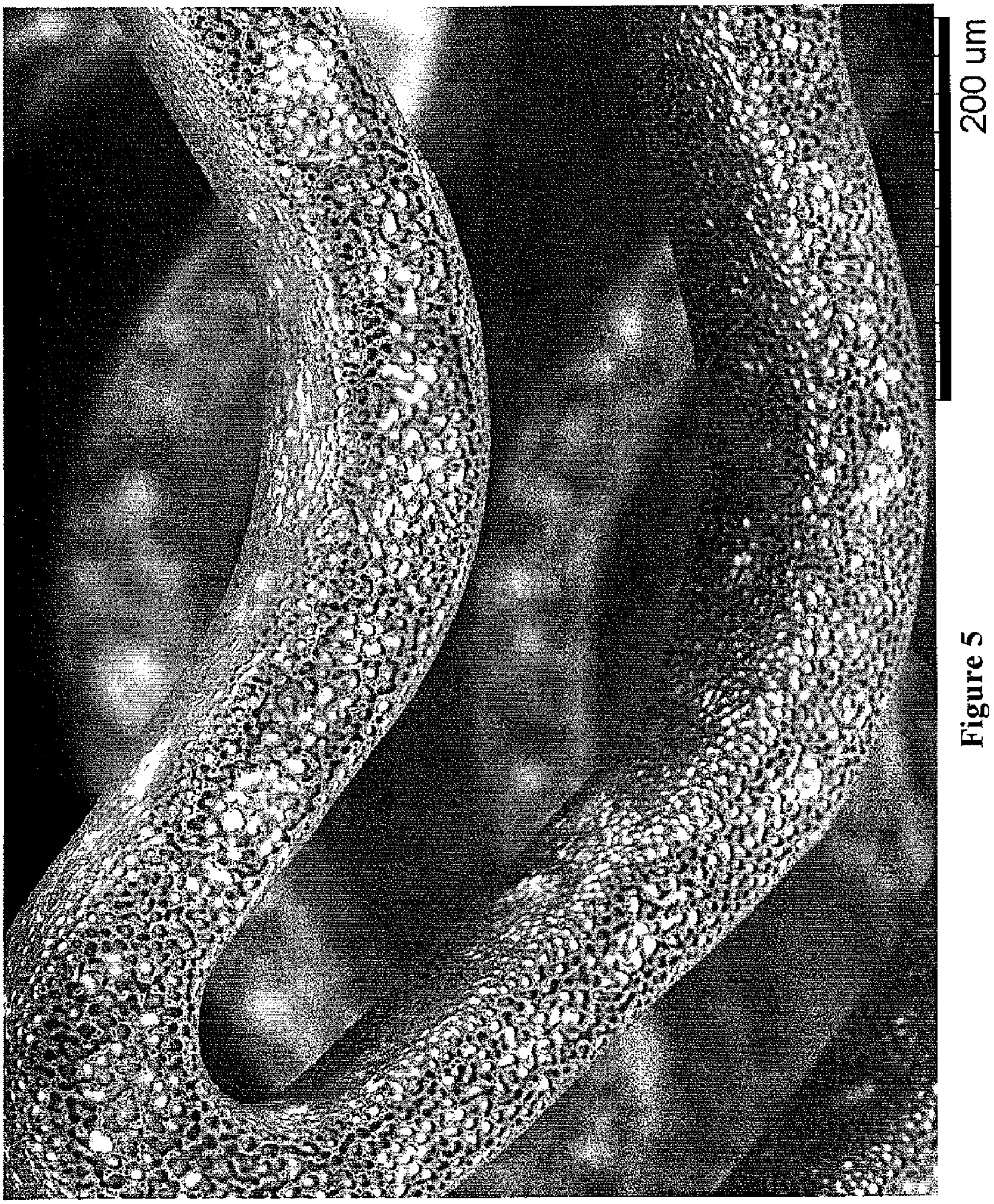
FIG. 5 is a scanning electron micrograph showing a magnified portion of an expandable vascular stent with a textured drug coating according to the invention.

FIG. 5 of the drawings shows a scanning electron micrograph of a textured surface multi-layer drug coated expandable vascular stent fabricated using the systems and methods of this invention. This drug eluting stent has favorable elution and coating durability properties compared to other drug coated stents without the necessity of employing a polymer binder or matrix to retain the drug.

Figure 6:
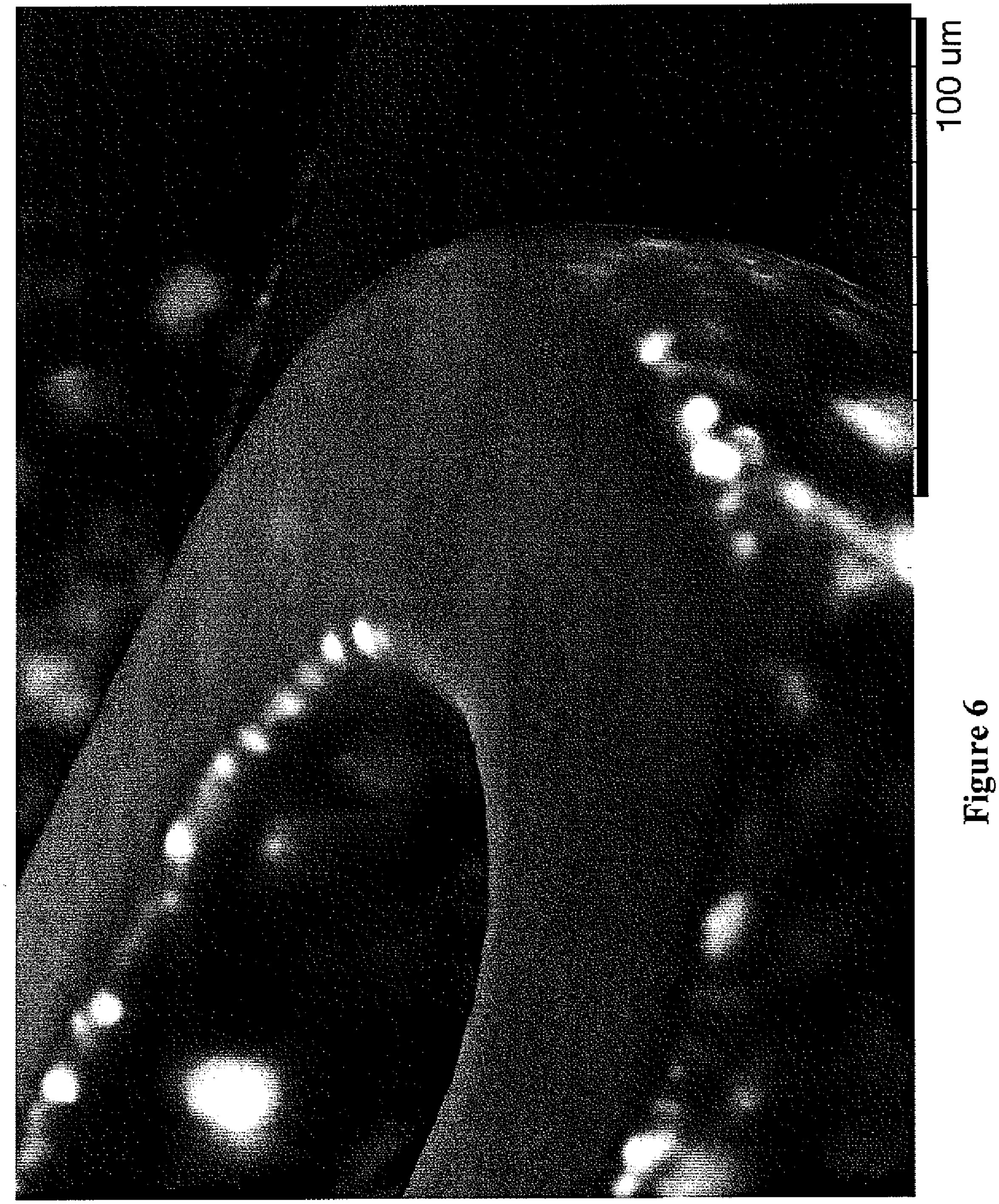
FIG. 6 is a scanning electron micrograph showing a magnified portion of an expandable vascular stent with a smooth drug coating according to the invention.

FIG. 6 of the drawings shows a scanning electron micrograph of a smooth surface multi-layer drug coated expandable vascular stent fabricated using the systems and methods of this invention. This drug eluting stent has favorable elution and coating durability properties compared to other drug coated stents without the necessity of employing a polymer binder or matrix to retain the drug.

When even more control over the elution rate is desired, the elution rate may be modified by incorporating a non-polymer material in the drug coating that affects the elution rate of the coating. Such a material would preferably serve to retard the elution of the drug to provide an extended period of medical activity of the drug when the drug eluting device is implanted into a mammal. If (for example without limitation) the therapeutic agent in the drug is particularly soluble in mammalian body fluids, or when a particularly long elution time is required for best therapeutic effectiveness, it is desirable to extend the elution time (and/or decrease the elution rate) of the drug in the drug coating on the drug eluting device by incorporating an elution-retarding material in the drug coating. This may be accomplished by incorporating the elution-retarding material in the drug-solvent solution prior to spraying onto the drug eluting device. Furthermore, when multi-layer coatings are formed, the relative mixture of drug and elution-retarding material in each layer may be selected to tailor the elution rate profile with time. Alternatively, rather than mixing the drug and elution-retarding material in each layer, drug coating layers may alternate with one or more elution-retarding material layers.

Suitable elution-retarding materials are preferably biocompatible with mammalian tissues and fluids, medically safe, and are preferably soluble in the solvent used for forming a drug spray solution for spray coating as described hereinbefore (except in cases where drug and elution-retarding material are applied in alternating layers which thus may employ different solvents). For example, certain fat-soluble mammalian trace nutrients can be beneficially employed as elution-retarding materials. Two preferred examples are vitamin E and vitamin A.

In an exemplary case, drug eluting expandable coronary stents were prepared with drug coatings according to apparatus and techniques disclosed hereinbefore and subsequently elution measurements were made on the coated stents. For each case, the drug employed was rapamycin and the solvent employed was THF. In the cases where an elution-retarding material, alpha-tocopherol (vitamin E) was used, it was mixed 7.5% (by weight) with the rapamycin prior to solution of the mixture in THF. The drug (and/or drug plus elution-retarding material) coatings were applied to the stents using the process described in Table 2, Case 6, above to produce coatings. In Case A, a single thick coating of rapamycin plus alpha-tocopherol (vitamin E) was formed on the stent by repeated vacuum spraying, and without any GCIB irradiation. In Case B and in Case C, respectively, five layer coatings of rapamycin and rapamycin plus alpha-tocopherol (vitamin E) were applied and each layer was GCIB irradiated. The coated stents were elution-tested by measuring weight loss resulting from immersion in deionized water at discrete times following initial immersion.

Table 3 shows the elution-testing results. In both cases where the coatings were GCIB irradiated, the elution times were extended in comparison to the un-irradiated case, but the longest elution time was demonstrated in the case (Case C) where GCIB irradiation and a non-polymer elution-retarding material were both employed.

TABLE 3

| Case | Number of Layers | % (weight) vitamin E | GCIB Dose per Layer | Initial Load (μg) | Elapsed Elution Time (hr) | Amount Eluted (μg) | % Eluted | Remaining Load (μg) |
|---|---|---|---|---|---|---|---|---|
| A | 1 | 7.5 | 0 | 17 | 0 | 0 | 0 | 17 |
| | | | | | 17 | 14 | 82 | 3 |
| | | | | | 41 | 0 | 82 | 3 |
| B | 5 | 0 | $10^{15}$ | 18 | 0 | 0 | 0 | 18 |
| | | | ions per | | 41 | 4 | 22 | 14 |
| | | | $cm^2$ | | 70 | 4 | 44 | 10 |
| | | | | | 135 | 7 | 83 | 3 |
| | | | | | 230 | 0 | 83 | 3 |
| C | 5 | 7.5 | $10^{15}$ | 15 | 0 | 0 | 0 | 15 |
| | | | ions per | | 41 | 3 | 20 | 12 |
| | | | $cm^2$ | | 70 | 1 | 27 | 11 |
| | | | | | 135 | 3 | 47 | 8 |
| | | | | | 230 | 3 | 67 | 5 |

Although the process of forming a drug coated medical device with a GCIB irradiated drug coating incorporating a non-polymer elution-retarding material has been described in terms of vacuum spray coating the drug and/or elution-retarding material onto the medical device prior to irradiation, it will be readily recognized by those skilled in the arts that the coating of the medical device could alternatively be done by dipping the medical device in a solution containing the drug (and/or) elution retarding material, drying the coating to remove solvent, and then irradiating the resulting dry coating. The process can be repeated for multi-layer coatings.

Although the invention has been described with respect to various embodiments comprising expandable vascular stents, it will be realized by those skilled in the arts that though the invention is particularly useful for coating stents with drugs, it is not limited to application to stents and may be applied to a wide range of medical devices intended for implant into the body or tissues of a mammal. Although the terms "drug" and "drug coating" have been used and examples of rapamycin and paclitaxel have been given, it is intended that the term "drug" includes all forms of therapeutic agents that may beneficially be employed as coatings on medical devices intended for implant, including organic and inorganic compounds, provided however that they must be soluble or able to form stable suspensions or dispersions so as to form a sprayable liquid. A few examples, not for limitation, include rapamycin, paclitaxel, zotarolimus, their analogs and derivatives. The term "drug" is also intended to include drug mixtures and to include the optional presence of other agents intended to modify the solubility or stability of a therapeutic agent. The term "vitamin E" is intended to include, without limitation, alpha-tocopherols, gamma-tocopherols, delta-tocopherols, and other tocopherols. The term "vitamin A" is intended to include, without limitation, retinol and other retinoids. It should be realized this invention is also capable of a wide variety of further and other embodiments within the spirit and scope of the foregoing disclosure and the appended claims.

What is claimed is:

1. A method of coating a medical device with a drug, comprising the steps:

a) disposing the medical device in a vacuum environment;

b) providing at a pressure above atmospheric pressure, a solution of a drug solute dissolved in a liquid solvent;

c) spraying at least one pulse of the solution onto a surface of the medical device, in the vacuum environment, to form a solution coating on at least a portion of the medical device;

d) vacuum treating the solution coating after the step of spraying to remove the solvent and leave a drug coating on the medical device; and e) treating the drug coating to enhance adhesion of the drug coating to the medical device surface and/or to retard drug transfer from the drug coating under intended usage conditions.

2. The method of claim 1, wherein the steps of spraying and vacuum treating the solution coating are repeated prior to the step of treating the drug coating.

3. The method of claim 1 further comprising repeating at least once, the steps c), d), and e) to thicken the drug coating.

4. The method of claim 1, wherein the step of vacuum treating includes operating a vacuum pump connected to the vacuum environment to automatically reestablish vacuum pressures after each spraying pulse.

5. The method of claim 1, wherein the step of spraying is adapted to deliver the solution to the medical device with only limited evaporation of the solvent.

6. The method of claim 1, wherein the step of spraying is adapted to retain substantially all of the solute in solution until it reaches the medical device.

7. The method of claim 1, wherein treating the drug coating step comprises ion irradiating the drug coating in the vacuum environment and in a manner to reduce a drug elution rate of the drug coating and/or to improve the adhesion of the drug coating to the medical device.

8. The method of claim 7, wherein the step of ion irradiating comprises GCIB irradiation.

9. The method of claim 1 further comprising: the step of cleaning the medical device by gas cluster ion beam processing in a vacuum environment prior to the spraying step.

10. The method of claim 1 wherein substantially all medical device surface portions intended for mammalian body contact are thus coated with drug coating.

11. The method of claim 1 wherein the medical device is a stent.

12. The method of claim 1, wherein the drug solution comprises an elution-retarding material solute.

13. The method of claim 12, wherein the elution-retarding material solute includes one or more of a vitamin, a tocopherol, retinol, a retinoid, and a fat soluble biocompatible material.

14. A drug coated medical device as made by the method of claim 1.

15. An apparatus for coating a medical device with a drug comprising:

a vacuum chamber adapted to be operable at a pressure below 100 mtorr;

means for holding the medical device in the vacuum chamber;

means for pulse spraying a solution of the drug at a pressure above atmospheric pressure onto a surface of the medical device in the vacuum chamber to form a solution coating;

vacuum producing means for providing a reduced pressure in the vacuum chamber before and after pulse spraying for evaporating solvent from the solution coating to form a drug coating; and means for introducing a gas cluster ion beam into the vacuum chamber adapted to irradiate at least a portion of the drug coating with gas cluster ions.

16. The apparatus of claim 15 wherein the means for holding, means for pulse spraying and means for introducing are constructed and adapted for full surface coating of the medical device.

17. The apparatus of claim 15, further comprising control means adapted to cause a sequence of spray pulses of the solution separated by evaporation periods for evaporating solvent from the solution coating from each spray pulse.

18. The apparatus of claim 17, wherein the control means is further adapted for causing sequential layers of drug coating to be separately irradiated with the gas cluster ion beam.

19. The apparatus of claim 15, wherein the means for spraying is adapted to deliver the solution to the medical device with only limited evaporation of the solvent.

20. A drug coated medical device, comprising a drug coating having a textured surface that is GCIB irradiated.

21. The device of claim 20, further comprising an elution-retarding material in the drug coating, wherein the coating includes one or more layers, and further wherein the drug and the elution-retarding material are either contained in the same layer or in separate layers.

22. The device of claim 20, wherein the elution-retarding material includes one or more of a vitamin, a tocopherol, retinol, a retinoid, and a fat soluble biocompatible material.

23. The device of claim 20, wherein the drug coating has a textured surface prior to GCIB irradiation.

24. The method of claim 1, wherein the vacuum environment is at a pressure of 100 mtorr or less immediately prior to the spraying step.

25. The method of claim 1, wherein the vacuum environment is at a pressure of 35 mtorr or less immediately prior to the spraying step.

26. The method of claim 24 further comprising the step of delaying to permit the vacuum environment to recover to a pressure of 100 mtorr or less after the vacuum treating step and before the treating the drug step.

27. The method of claim 6, wherein the steps of spraying and vacuum treating form a textured surface on the drug coating.

28. The apparatus of claim 15, wherein the drug coating has a textured surface.

* * * * *